US011232870B1

(12) United States Patent
Shaashua et al.

(10) Patent No.: US 11,232,870 B1
(45) Date of Patent: Jan. 25, 2022

(54) COMMUNICABLE DISEASE PREDICTION AND CONTROL BASED ON BEHAVIORAL INDICATORS DERIVED USING MACHINE LEARNING

(71) Applicant: Neura Labs Ltd., Herzeliya (IL)

(72) Inventors: Triinu Magi Shaashua, Sunnyvale, CA (US); Amit Hammer, Herzeliya (IL); Ori Shaashua, Sunnyvale, CA (US)

(73) Assignee: Neura Labs Ltd., Herzeliya (IL)

( * ) Notice: Subject to any disclaimer, the term of this patent is extended or adjusted under 35 U.S.C. 154(b) by 0 days.

(21) Appl. No.: 17/116,970

(22) Filed: Dec. 9, 2020

(51) Int. Cl.
*G16H 50/80* (2018.01)
*G06N 20/00* (2019.01)
*G16H 50/30* (2018.01)
*G16H 50/70* (2018.01)

(52) U.S. Cl.
CPC ............. *G16H 50/80* (2018.01); *G06N 20/00* (2019.01); *G16H 50/30* (2018.01); *G16H 50/70* (2018.01)

(58) Field of Classification Search
CPC .......... G16H 5/80; G16H 50/30; G16H 50/70; G06N 20/00
See application file for complete search history.

(56) References Cited

U.S. PATENT DOCUMENTS

| 10,303,843 | B2 * | 5/2019 | Bitran | G16H 50/70 |
| 2009/0265106 | A1 | 10/2009 | Bearman et al. | |
| 2011/0093249 | A1 * | 4/2011 | Holmes | G16H 50/70 |
| | | | | 703/6 |
| 2014/0113267 | A1 * | 4/2014 | St. Hilaire | G06Q 30/0203 |
| | | | | 434/362 |
| 2014/0155705 | A1 * | 6/2014 | Papadopoulos | A61B 5/0004 |
| | | | | 600/301 |
| 2015/0100330 | A1 * | 4/2015 | Shpits | G16H 50/80 |
| | | | | 705/2 |
| 2017/0024531 | A1 * | 1/2017 | Malaviya | G16H 40/63 |
| 2018/0181714 | A1 * | 6/2018 | Pillarisetty | G16H 50/30 |
| 2019/0209022 | A1 * | 7/2019 | Sobol | A61B 5/7435 |
| 2020/0135337 | A1 * | 4/2020 | Athey | G16H 50/20 |
| 2020/0294680 | A1 * | 9/2020 | Gupta | G06N 7/005 |

OTHER PUBLICATIONS

Gollier, Christian; Gossner, Oliver: Group testing against COVID-19, EconPol Policy Brief, No. 24, ifo Institute—Leibniz Institute for Economic Research at the University of Munich, Munich, Mar. 20, 2020, pp. 1-11 (Year: 2020).*

* cited by examiner

*Primary Examiner* — Evangeline Barr
(74) *Attorney, Agent, or Firm* — Perkins Coie LLP; Brian Coleman; Jingyuan Huang

(57) ABSTRACT

Methods, apparatus, and systems for predicting and controlling communicable diseases are disclosed. In one example aspect, a method for predicting a communicable disease includes receiving, for each member of a community, multiple data streams associated with the member from multiple sensor devices, and computing, based on a social or locational relationship between the member and other entities in the community and a timeline of activities performed by the member according to the timestamp for each data packet, a list of behavioral indicators for the community indicating a current state of the communicable disease using one or more machine learning models.

28 Claims, 13 Drawing Sheets

COMMUNICABLE DISEASE PREDICTION AND CONTROL BASED ON BEHAVIORAL INDICATORS DERIVED USING MACHINE LEARNING

BACKGROUND

A communicable disease is one that is spread from one person to another through a variety of ways, such as contact with blood and bodily fluids or breathing in an airborne virus. From the coronavirus-cased COVID-19 to influenza, Lyme disease malaria and Ebola, outbreaks of infectious diseases can have an extraordinary impact on human health. Preventing the spread of disease is at the heart of public health work. Yet, predicting how the disease spreads in communities, thereby facilitating the control thereof, remains to be a challenge.

DETAILED DESCRIPTION

Figure 1:
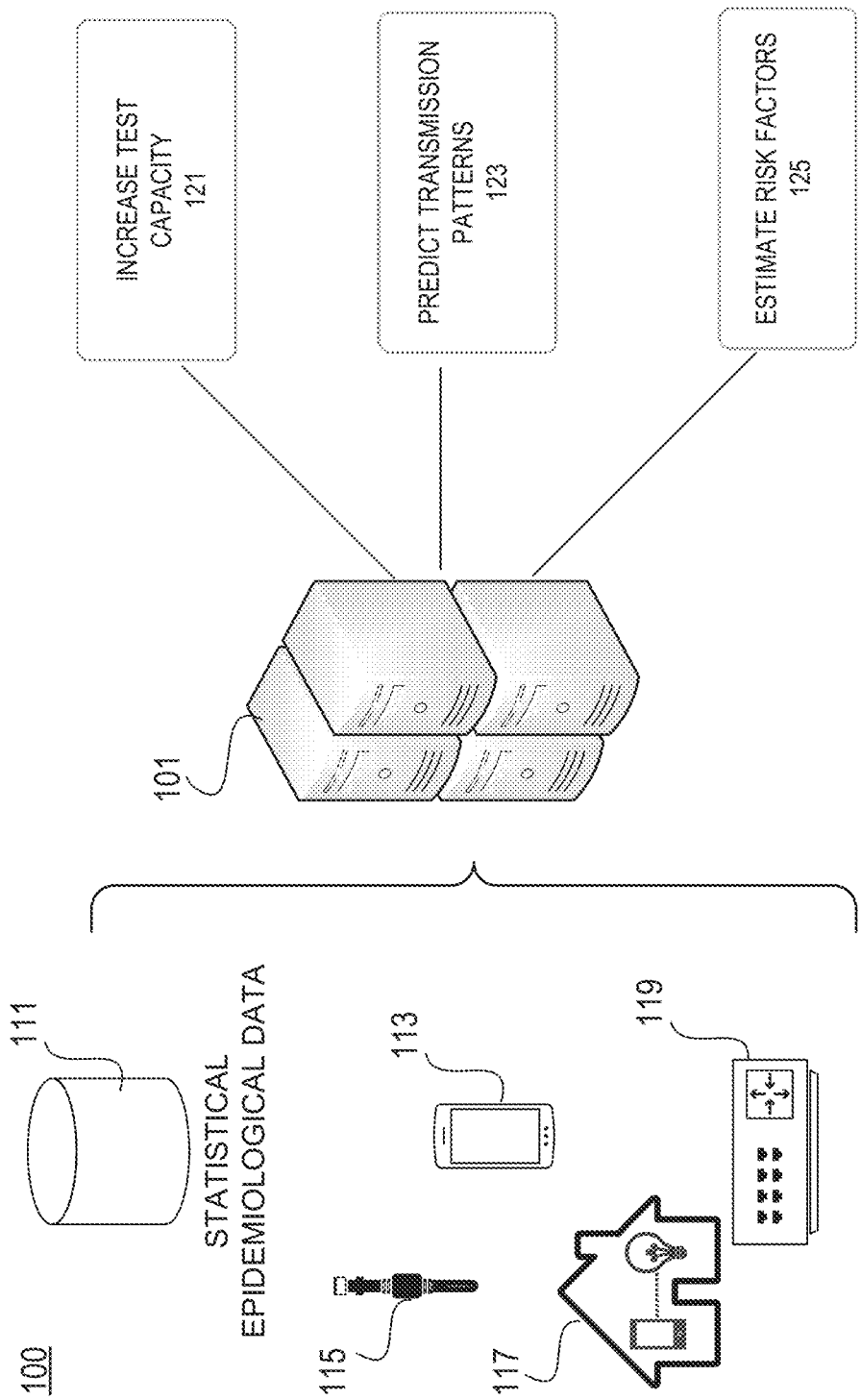
FIG. 1 is a schematic diagram of an example architecture of a prediction and control system in accordance with the present technology.

Communicable diseases pose risks to societies in a variety of ways. The recent COVID-19 pandemic has brought big challenges to communities and healthcare professionals. Many countries have implemented various forms of "lockdowns" to combat the spread of COVID-19. Many tracking and projection models have been developed to provide an insight into the state of the disease transmission. For example, the United States Centers for Disease Control and Prevention (CDC) received forecasts of COVID-19 from 47 modeling groups. The CDC also adopts an ensemble forecast that combines the multiple forecasts to improve accuracy of the prediction over a period of time. However, many of these models examine and forecast death case numbers exclusively; few takes into account the impact of behavioral changes on the spread of communicable diseases.

Continuous lockdowns are not sustainable in many communities, and countries are investigating exit strategies from the lockdowns to be able to successfully control transmission. Once the lockdown measures are lifted, testing, transmission predictions, and proper local measures are key components in the exit strategies to ensure that the spread of the disease is under control while communities can go back to normal levels of activities. These key components need to be linked with agile technical systems to facilitate transmission of case data and management of multiple data streams with seamless interoperability. Furthermore, after the lockdown measures are lifted, transmission of communicable diseases is largely dependent on how individuals interact with each other within communities. Models that take a limited number of input data types (e.g., death numbers) cannot provide sufficient guidance for communities to properly implement the exit strategies.

This patent documents discloses techniques that can be implemented in various embodiment to leverage behavioral information in disease prediction and control. The disclosed techniques not only examine statistical epidemiological data (e.g., testing data, number of infected and/or death cases) but also analyze behavioral intelligence by reviewing population behavioral data collected from a variety of sources, such as Internet-of-Thing (IoT) devices associated with community members, the corresponding routers, gateways, access points and base stations. By identifying the physical and social relationships between different entities in the communities, the system can compute different types of predicators to provide meaningful predictions of disease transmission, as well as to identify safe neighborhoods and transmission hotspots, thereby enabling governments at different levels to proactively mitigate the spread of the diseases so as to safely reopen the communities. The disclosed techniques can be utilized to make decisions, such as where to set new testing or screenings sites based on risks of new outbreaks, how to provide additional medical resources when the predicted hospitalization needs increase, whether to close or open markets, shopping centers, or living areas, and what type of communications is needed to inform community members of activities across the borders.

In some embodiments, the disclosed techniques can be implemented as a disease prediction and control system. FIG. 1 is a schematic diagram of an example architecture of a prediction and control system 100 in accordance with the present technology. As shown in FIG. 1, the system receives input data streams from a variety of sources, including but not limited to statistical epidemiological data 111 (e.g., testing results, infected cases, number of deaths) and data from various types of mobile sensors, such as smart phones 113, smart watches 115, and smart home devices 117. Additional data sources include routers 119, access points, gateways, and/or base stations that provide connectivity to the mobile sensors. The input data streams can include information such as geolocations, personal activities, health measurements, WiFi or Bluetooth connection states, device charging status, etc. Alternatively, or in addition, data from the corresponding sensors can be obtained from third-parties (e.g., via purchase). The identities of the community members remain anonymous in the input date streams to protect privacy of the individuals. The system then derives predictors that can be used to increase test capacity 121, predict transmission pattern in communities 123, and estimate risk factors at the community level 125.

In some embodiments, the prediction and control system includes a decision engine 101 that is configured to receive the input data streams. The decision engine 101 can receive periodical statistical epidemiological data updates from government databases at different geographical levels (e.g., different zip codes, counties, states). For example, the statistical epidemiological data can be updated daily to reflect changes in the number of infected and deceased cases.

As compared to epidemiological data collection from government databases, data collection from various types of mobile sensors needs to be performed at a higher frequency to accurately reflect behavioral changes of individuals in different communities. However, high-frequency data collection can result in power consumption issues on mobile sensors and put a strain on the processing power of the decision engine. In order to achieve the right balance between the collection frequency and the consumption of power/computing resources, the decision engine can configure the manner in which data should be collected and inform the mobile sensors how and when to report the relevant data.

Figure 2:
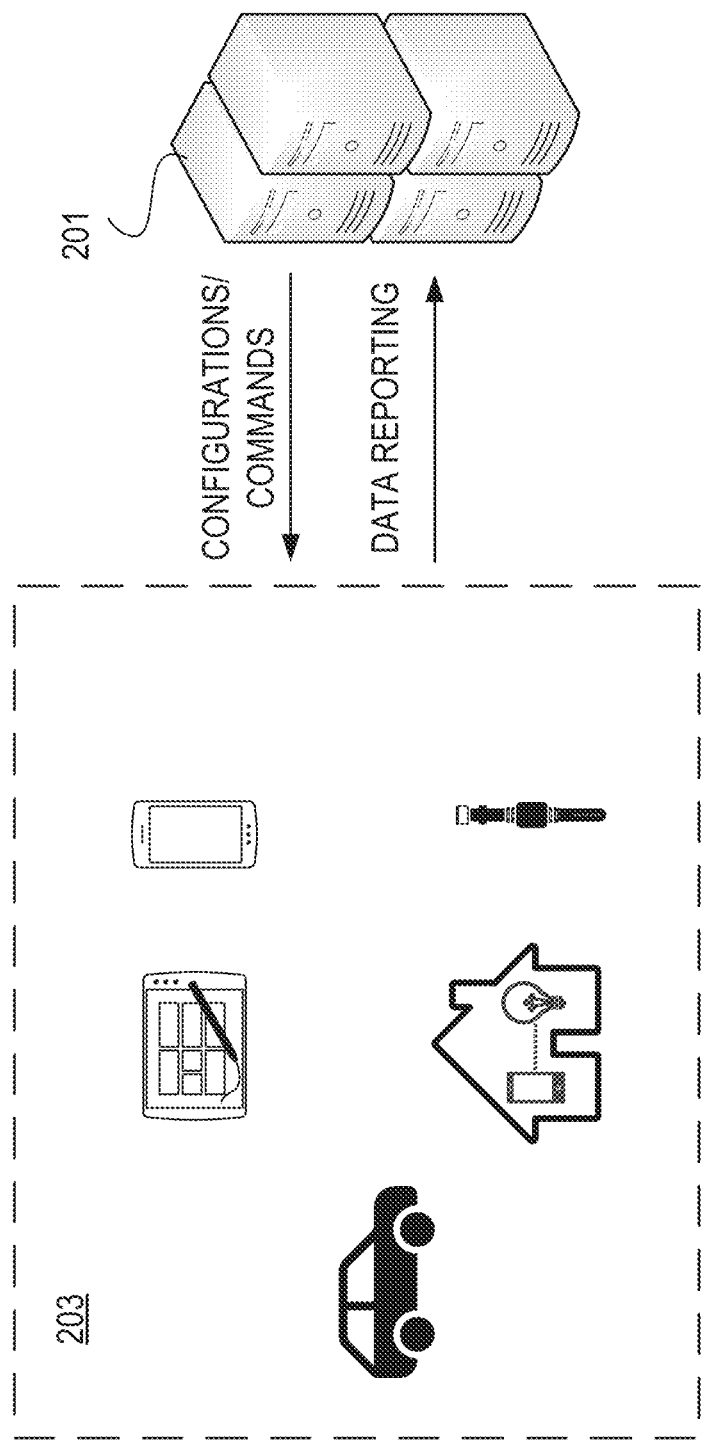
FIG. 2 illustrates an example of collection configuration and data reporting in accordance with the present technology.

FIG. 2 illustrates an example of collection configuration and data reporting in accordance with the present technology. In this example, the decision engine 201 uses a machine learning model to determine the manner of data collection from mobile sensors 203. The machine learning model can be trained using a combination of offline and online training techniques. Once the machine learning model is sufficiently trained, it can be used to determine different data types needed for one or more types of mobile sensor devices. Certain types of devices, such as mobile phones, can be used to provide different types of data streams, including but not limited to geolocation, connectivity data with routers, access points, or gateways, gyrometer data or other activity-related data. For specific types of devices (e.g., smart home thermometers), on the other hand, the model can eliminate some data streams (e.g., charging status) from data collection because those types of data streams do not convey meaning behavioral information about the member. The model can further configure the collection frequency of each type of data streams. The collection frequency can be periodic and/or aperiodic. For example, geolocation data can be collected periodically (e.g., every hour) from a cell phone of a member. If the use member also possesses a vehicle, the model can reconfigure the collection frequency of geolocation data on the cell phone and use aperiodic or periodic geolocation data collected from the vehicle instead.

The decision engine 201 sends the configurations determined by the machine learning model to the mobile sensors 203. If periodic data collection is configured, the mobile sensors 203 can invoke function calls for data reporting periodically in a manner that is consistent with the configurations. In some embodiments, aperiodic data collection is needed (e.g., for event-driven data collection). The events that trigger aperiodic data collection can be included in the configurations from the decision engine 201. The decision engine 201 can also send separate commands to the mobile sensors to trigger aperiodic data collection. For example, a vehicle can be configured to report geolocation data upon ignition. Once the decision engine 201 detects data reports from the vehicle, it can send commands to the cell phone that is associated with the same user to reduce the collection frequency and/or temporarily disable geolocation collection from the cell phone. Upon being notified that the user has left the vehicle, the decision engine can send another set of commands to trigger the cell phone to report data according to the previously configured frequency. The change of data collection frequency remains completely invisible to the user.

Each data report (either periodic or aperiodic) is associated with one or more timestamps. For example, a data report can be associated with a collection timestamp to allow the decision engine to order the data packets received for subsequent processing. The data report can also be associated with a transmission timestamp to allow data re-transmissions and/or ordering should the connection with the decision engine fails or becomes unstable.

Figure 3:
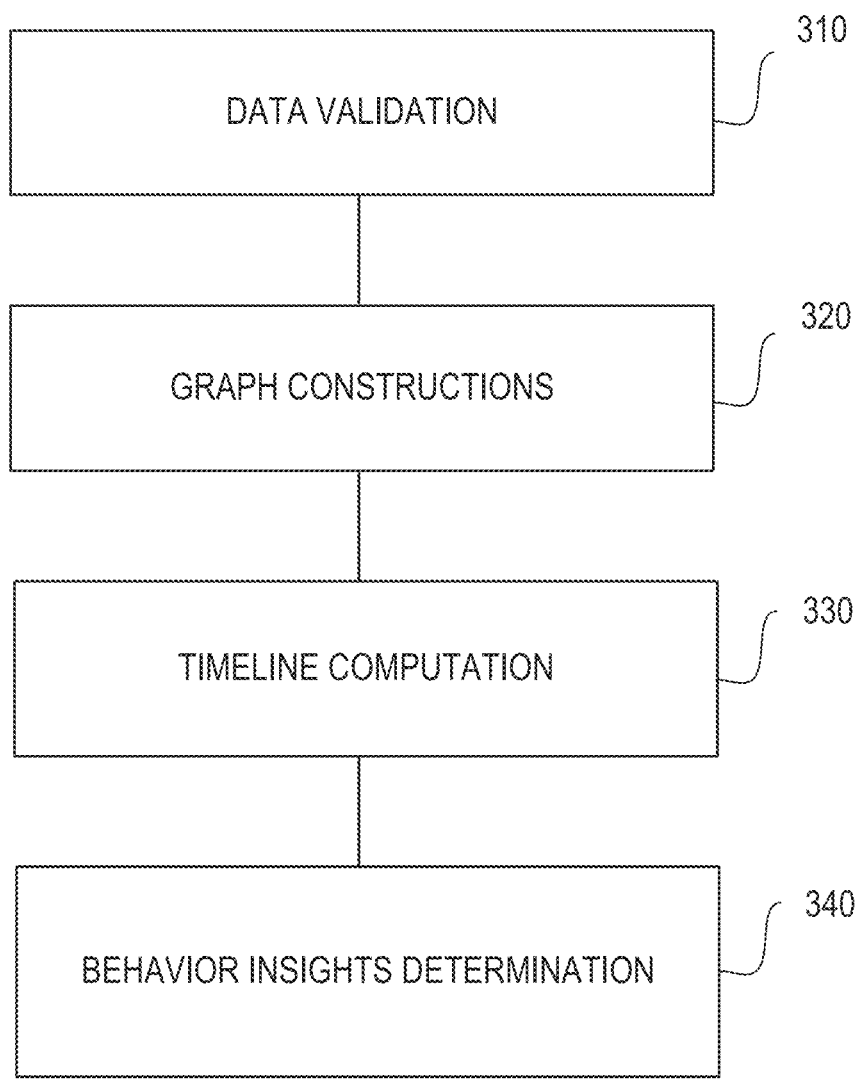
FIG. 3 is a flow chart representation of example operations performed by a decision engine in accordance with the present technology.

After the decision engine receives the input data streams, it performs several processing operations to generate behavioral insights related to disease transmissions. FIG. 3 is a flow chart representation 300 of example operations performed by a decision engine in accordance with the present technology. Upon receiving the variety of input data streams, the decision engine performs, at operation 310, data validation to ensure the quality of data used for subsequent operations. During data validation, data reports that have invalid fields (e.g., out-of-range values, missing fields, invalid future timestamps) are first discarded. The decision engine then examines the accuracy of data. For example, a JavaScript Objection Notation (JSON)-formatted geolocation includes a field that indicates the accuracy of the location. If the accuracy is lower than a predefined or configurable threshold, the data can be discarded for subsequent processing.

The decision engine also examines the configured collection frequency and the actual collection frequency of the data packets. In some scenarios, the connection between a mobile sensor and the decision engine may not be stable, resulting in a loss of data packets. For example, a power outage can cut off the connection between a smart home sensor and the decision engine. The decision engine compares the timestamps of the collected data from the smart home sensor with the configured frequency to determine whether there is an excessive amount of data loss. If so, data packets from this particular sensor are discarded for subsequent processing within a certain time duration. Such decisions can also be fed back to the machine learning model discussed in connection with FIG. 2 to improve configuration settings for sensor devices.

For different types of data streams, different criteria can be used to determine the validity of the data. For example, for geolocation data, accuracy is assigned a larger weight in determining the validity of the data. For personal health related data (e.g., heart rate, body temperature measurements, prescription intake time), accuracy of the geolocation of the sensor source is not important. More weight is given to the frequency of the data collected and the precision of the data fields according to the data types.

Figure 4:
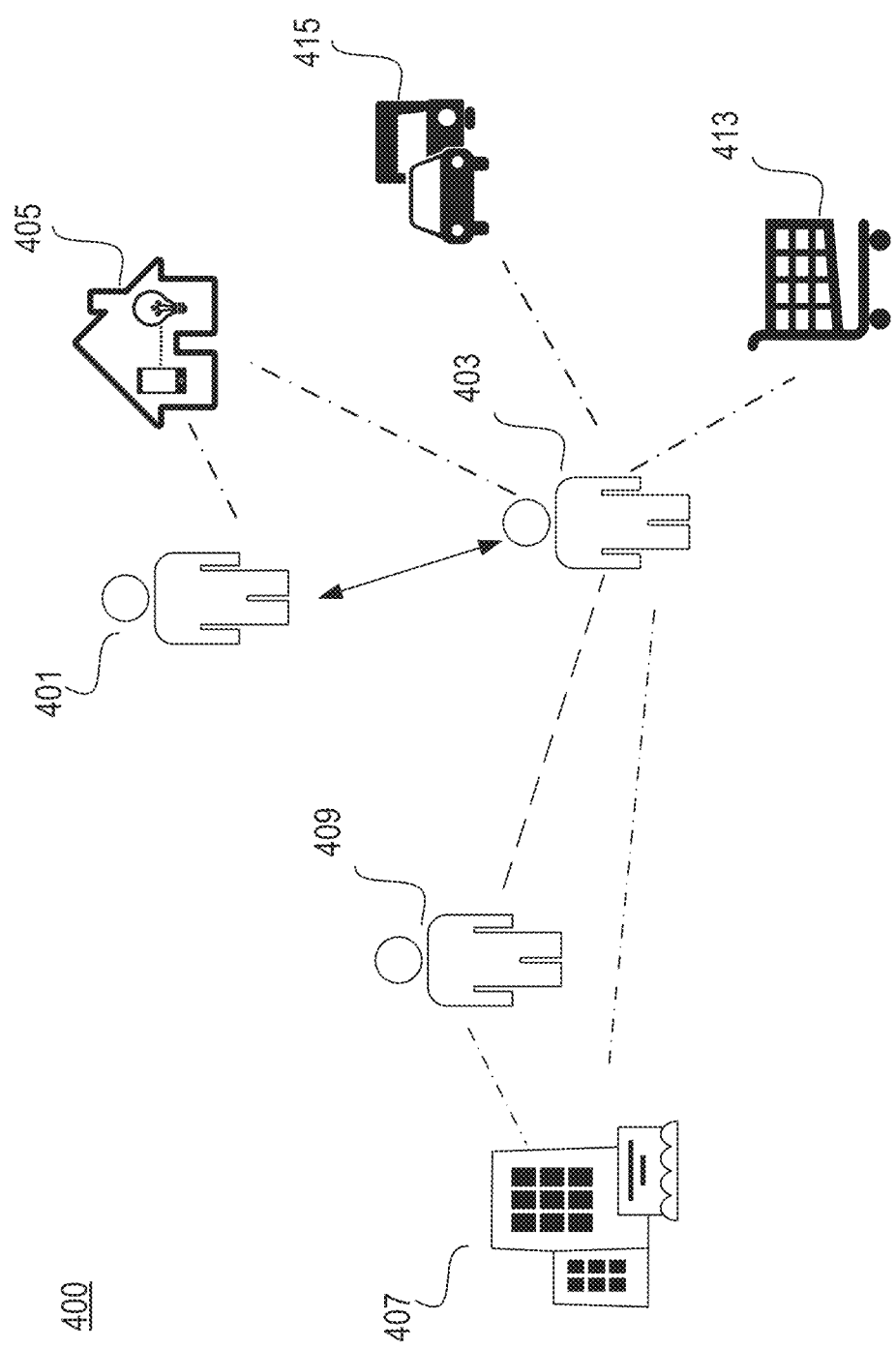
FIG. 4 illustrates an example entity graph in accordance with the present technology.

After the input date is validated, the decision engine consolidates the data based on the contextual information extracted from the data. In some embodiments, data can be aggregated into different contextual bins based on the correlation between the data. For example, data reported from an exercise tracker of a member can be correlated with data from heart rate monitor owned by the same member based on the shared known context of "health". The contextually consolidated data can be used to construct an entity graph, at operation 330, that represents social and physical relationships of the community members. FIG. 4 illustrates an example entity graph 400 in accordance with the present technology. Here, an entity can be a person in the community. An entity can also be an object, such as a house, a building, or a specific location that members visit.

As shown in FIG. 4, entity 401 (a community member Peter) is socially related to another entity 403 (his spouse Alicia). Both entities 401 and 403 (Peter and Alicia) have a locational relationship with entity 405 (a house) as their residence. Based on geolocation of the entities as well as network connection data (e.g., router model/location, the nature of connection data from the associated mobile devices), the decision engine can label entity 405 as Alicia and Peter's home. Peter (entity 401) is currently working from home and his activities are largely limited to the house, so he is not associated with other locational entities in the graph 400. For Peter, their house (entity 405) can also be labeled as workplace due to the nature of his connection data (e.g., the router can detect packets routing via a company virtual private network). Alicia (entity 403) is an essential worker who commutes to her workplace (entity 407). Based on her geolocation data from her mobile devices and data from her vehicle (entity 415), it can be established that she has a locational relationship with entity 407. Furthermore, when Alicia's mobile phone is connected to her company's WiFi network at the workplace (entity 407), the connection data can help indicate that entity 407 should be labeled as Alicia's workplace. Alicia is also socially related to her colleagues (e.g., entity 409). For example, transmissions between Alicia's devices and her colleagues' devices (e.g., air drop or text messages) can help establish their social relationship. On her way back home, Alicia can visit the grocery shop (entity 413). Her location data (e.g., from her mobile devices and the vehicle) as well as her payment information can establish a locational relationship between her and the shop (entity 413).

Referring back to FIG. 3, based on the timestamps of the data packets received by the decision engine, the decision engine can compute, at operation 330, a timeline of activities for each community member. For example, a member's daily activities and events can be completely or partially correlated together in the order of the time of the day. For example, based on the aggregated and consolidated data, the decision engine can determine the activity states of the user. The activity states can be associated with the corresponding time information (e.g., collection timestamps) to determine the timeline. In some embodiments, the decision engine uses multiple machine learning models to perform data consolidation and timeline construction. When outputs from different models indicate the member performs different activities at the same time (e.g., one model decides that the member is sleeping at time T while another model decides that the member is driving at time T), an additional post-processing machine learning model can be deployed to calculate the likelihood of each decision, thereby providing the final timeline of daily activities of the member.

Figure 5:
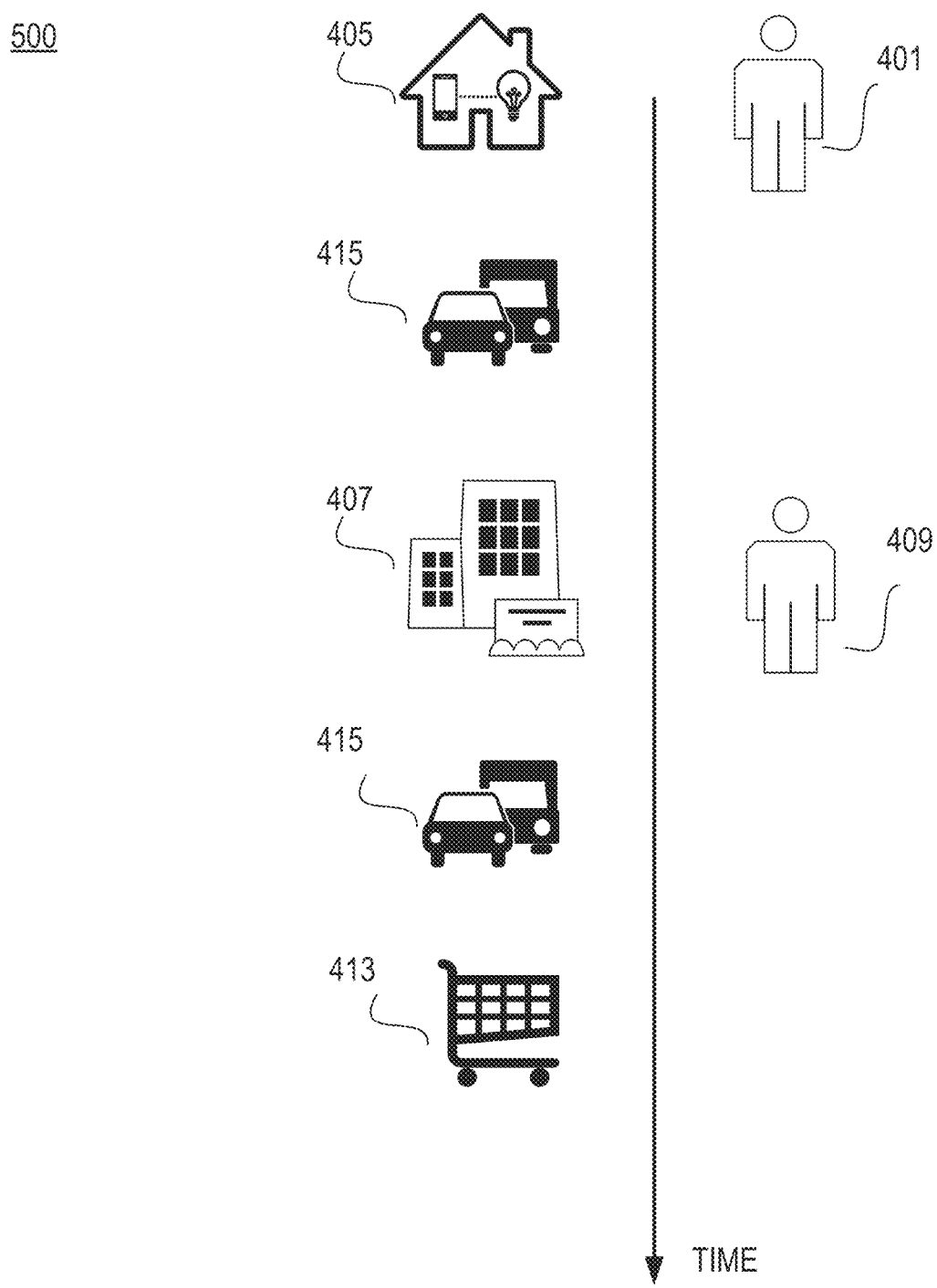
FIG. 5 illustrates an example timeline of an entity in accordance with the present technology.

FIG. 5 illustrates an example timeline 500 of an entity (e.g., Alicia) in accordance with the present technology. As shown in FIG. 5, Alicia (entity 403) interacted with Peter (entity 401) in their house (entity 405) in the morning, before she took her vehicle (entity 415) and drove to the workplace (entity 407). There, she interacted with her colleague (entity 409). After she completed her work, she drove the vehicle (entity 415) again to visit the grocery shop (entity 413).

Based on the entity graphs and the computed timelines of community members, as well as the statistical epidemiological data (e.g., testing results, infected cases, number of deaths), the decision engine can compute a list of behavioral indicators for each community (e.g., buildings, neighborhoods, zip codes, cities, counties) to allow efficient transmission prediction and control. For example, the decision engine can determine, for a particular place in a community, the number of encounters occurred in that place per day and the density of people at the place. As another example, the decision engine can derive, based on the distances between members and their homes, the number of commuters in a community and the percentage of people who spent a certain amount of time outside of their homes per day. The decision engine can further determine the origins and destinations when community members travel.

Figure 13:
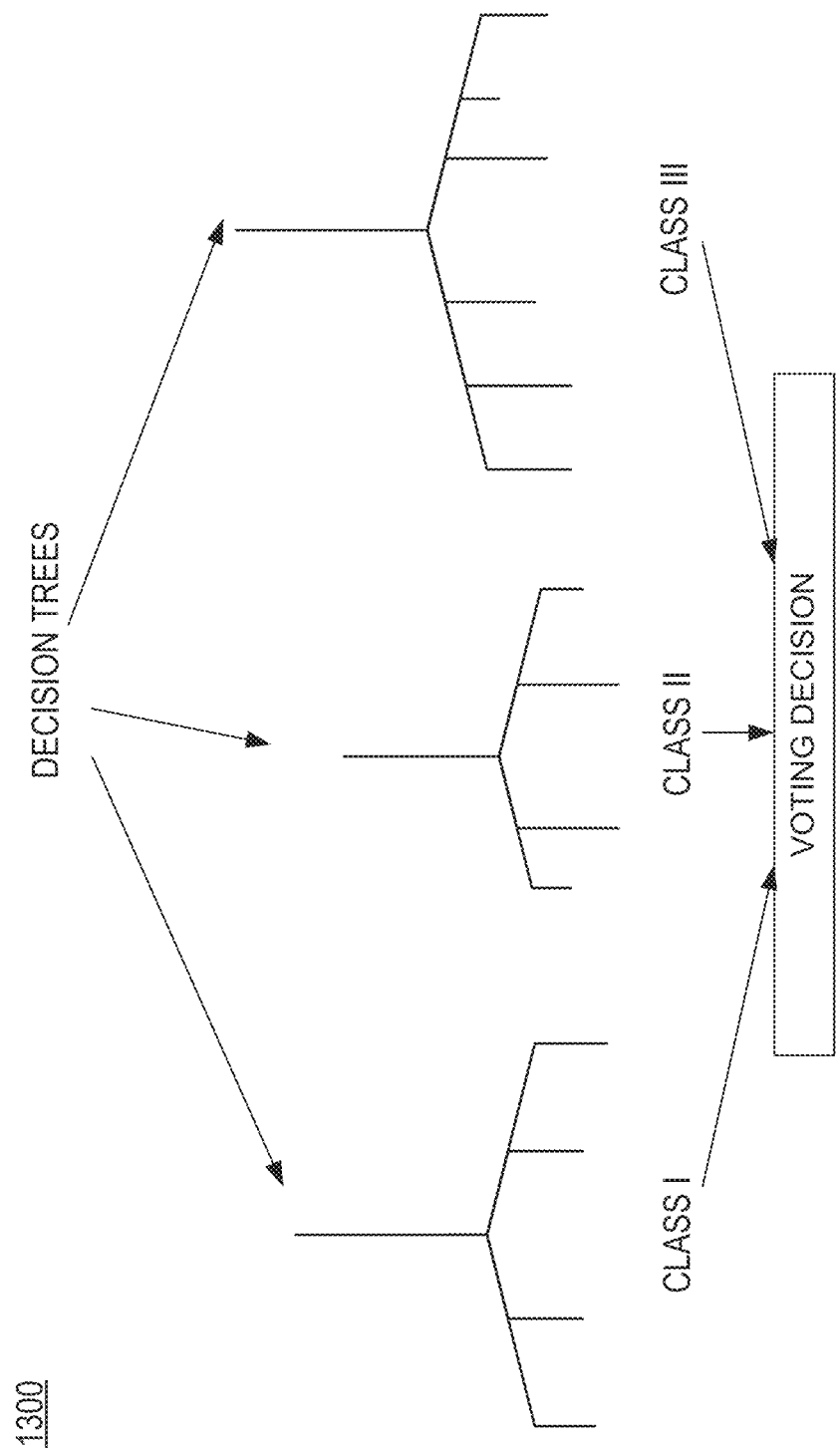
FIG. 13 illustrates an example tree structure in accordance with the present technology.

In some embodiments, one or more machine learning models can be implemented as part of the decision engine to facilitate the decision process. In some embodiments, machine learning techniques such as gradient boosting or random forest can be used to produces a prediction model in the form of an ensemble of decision trees. FIG. 13 illustrates an example tree structure in accordance with the present technology. During the training phase, the training algorithm selects a random sample with replacement of the training set and fits the ensemble of trees (classes I, II, or II) to these samples. After training, predictions for unseen samples can be made by weighting and normalizing the predictions from all the individual trees or by taking a majority vote from the trees. In some embodiments, the model uses a learning algorithm that selects a subset of the features. If one or a few features are very strong predictors for the target output related to disease transmissions, these features are selected in many of the decision trees, causing a strong correlation of the trees. The most correlative features are used to derive the results in different tree, which are then merged to produce a final value as a particular indicator.

Furthermore, because behavioral changes can often be observed in subpopulations (e.g., communities) within the whole population, techniques such as Gaussian Mixture Model (GMM) can be used to represent the presence of subpopulations within an overall population without the need for an observed data set to identify which sub-population it belongs. For example, a GMM can be extended to fit a vector of unknown parameters (e.g., collected data) to multivariate normal distributions, which is suitable for modeling population behaviors in various types of communities. It is noted that a combination of other types of machine learning models, such as neural networks or dimensionality reduction algorithms, can also be used in the decision engine to facilitate the decision-making process.

In some embodiments, the behavior indicators include, but not limited to, population density within a subarea of the community, social distancing index (e.g., how well people keep social distance from each other), percentage of people who work at home within the community, percentage of people who commute to workplaces within the community, average amount of time people spend outside of their homes, the number of people who commute between two particular locations, person-to-person encounter rate, likelihood of encountering an infected person, percentage of super spreaders in the community, percentage of social spreaders in the community, percentage of population who traveled outside of the community, quarantine index for members who have recently traveled, etc.

For example, referring back to FIG. 5, based on Alicia's timeline, the decision engine can determine that she is one of the people in her community (e.g., neighborhood, county, or state) who go back to work. The decision engine can aggregate timelines of community members to determine how many people are present at the same place around the same time, thereby calculating the population density for a particular location. The decision engine can determine how many people are working together with Alicia at the workplace, and how well the colleagues maintain the social distance when they interact with each other.

As another example, the decision engine can identify super spreaders based on an average number of places that a member visits per day. A threshold (e.g., top 10% of the population) can be provided to determine the number of individuals in a community that can be deemed as super spreaders.

In some embodiments, statistical epidemiological data can be used to further determine the behavior indicator. For example, epidemiological data from county database indicated that an anonymous member A who was diagnosed positioned visited Place P in one morning. Member A can be tagged as an infected/potentially infected member. Another anonymous member B, who was also present at Place A around the same time, can be tagged as a close contact or a potentially infected member. Based on the number of people who were also present at Place during the same period of time, the system can be used to determine whether a spreader event exists. Members who were present at a spreader event can be tagged as close contacts or potentially infected members. The decision engine can also tag certain people who came in contact with the spreader as risky members based on their health conditions and/or daily activities. The movement of the risky members can further indicate potential risks in other parts of the community.

Based on the derived behavioral patterns of community members and the statistical epidemiological data, the decision engine can also determine population movements between different areas (e.g., neighborhoods, cities, counties) and predict how the disease can transmit among communities due to such movements. Based on the prediction results, travel advisory can be issued for certain communities to control the spread of the disease.

In some embodiments, when insufficient data is available for a community (e.g., data from a community that is newly added to the system, a large number of members do not have mobile sensors to provide data), the system can leverage mathematical and/or statistical extrapolations based on its knowledge of similar communities to estimate the behavior patterns of community members. For example, the system may be able to collect data from around 20% of the population in a particular community. Based on the system's knowledge of other similar communities (e.g., similar size, similar population, etc.), the system can determine that the 20% of the population behavior is representative of the entire community. The system then proceeds to extrapolate the data to determine behavioral indicators for the community.

The example system described in connection with FIGS. 1-5 can be used in various applications for communicable disease prediction and control. Some example applications are discussed further in detail below.

Example Embodiment 1: Transmission Prediction

Figure 6:
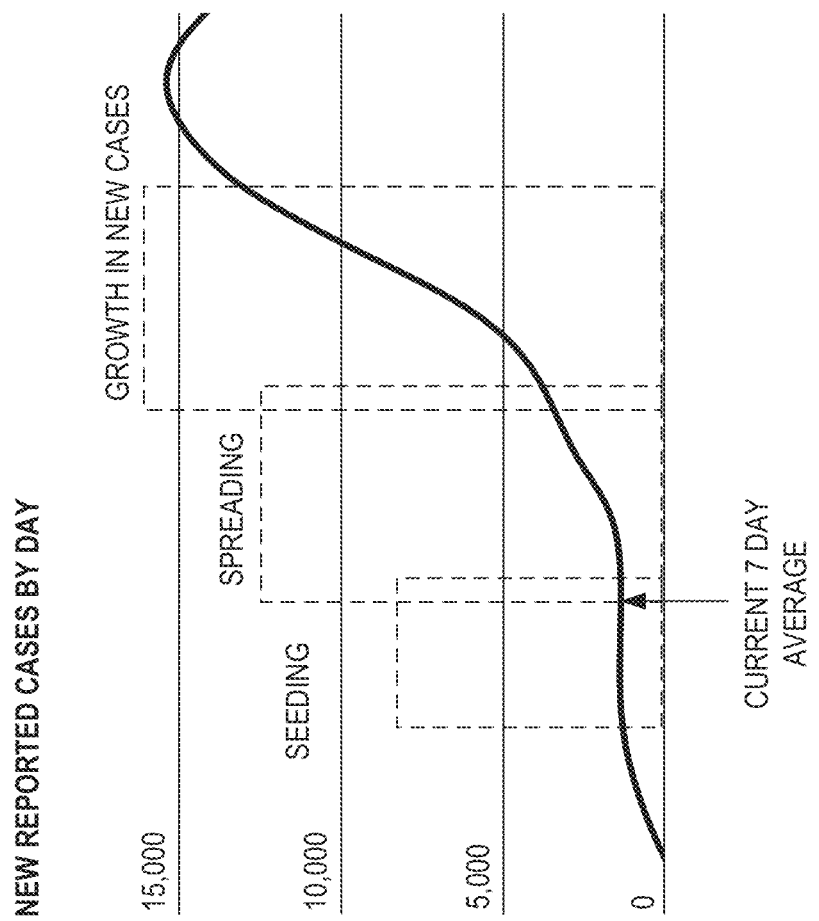
FIG. 6 illustrates an example prediction diagram generated by a prediction and control system in accordance with the present technology.

The prediction and control system can generate prediction trend based on the behavioral patterns of community members and the statistical epidemiological data. FIG. 6 illustrates an example prediction diagram 600 generated by a prediction and control system in accordance with the present technology. As shown in FIG. 6, the current statistical epidemiological data indicates that the 7-day average of the number of infected cases is relatively low. However, based on movement and activities of some of the infected super spreaders (e.g., the seeding stage), which has occurred prior to the current seven-day average, the model predicts that the community will soon face a spreading stage and a fast growth in new cases in the near future. Given such prediction, the community can adopt certain measures to minimize the spread of the disease and to avert the trend.

Example Embodiment 2: Risk Score Generation

The system can generate risk scores to indicate whether a community is a high-risk infection area. For the community, the system can determine two types of risk scores: current risk score and transmission risk score. Current risk score indicates the current state of a community. Transmission risk score indicates the likelihood of future transmission of the disease within the community.

In some embodiments, risk scores can be generated based on the transmission prediction results as discussed in Embodiment 1. For example, if a community is predicted to have a fast growth of new cases, such as shown in FIG. 6, the community is assigned a high transmission risk score even though the community may have a low current risk score.

Figure 7:
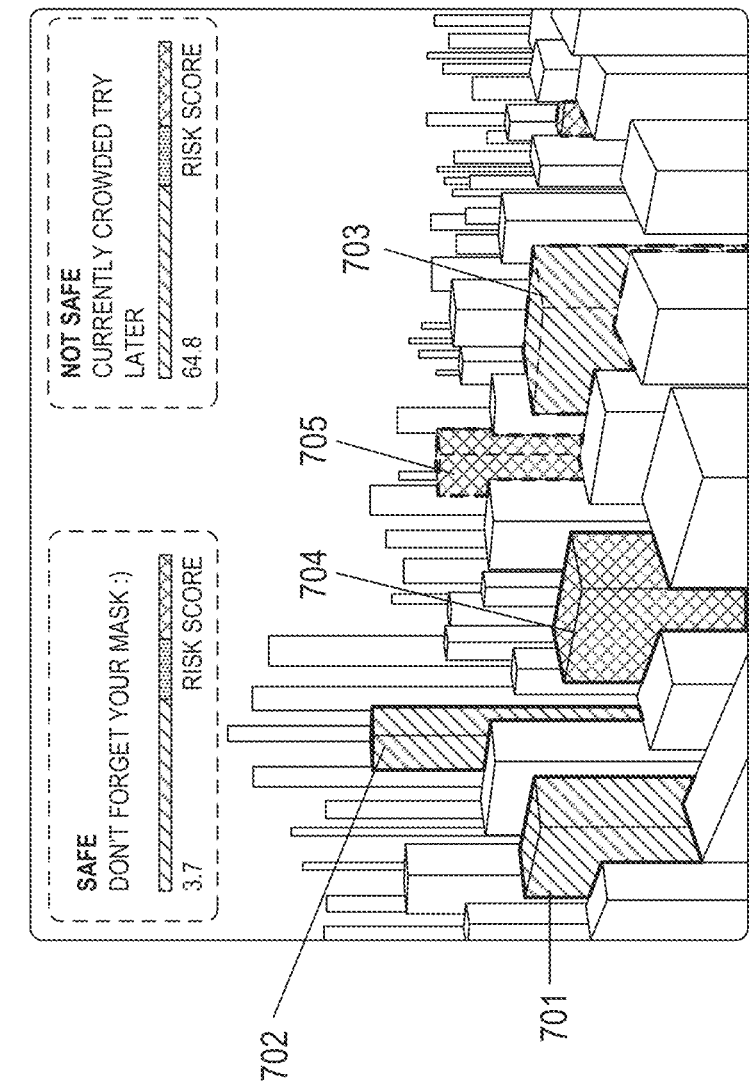
FIG. 7 illustrates an example visualization of risk scores for various buildings in a community in accordance with the present technology.

In some embodiments, the system can generate visualizations of the risk scores to help guide community members to determine whether it is safe to enter certain locations. FIG. 7 illustrates an example visualization of risk scores for various buildings in a community in accordance with the present technology. As shown in FIG. 7, buildings 701, 702 and 703 are shown as being low risk. In particular, building 703 (in dotted line) is given a risk score of 3.7, indicating that it is a safe location for people to enter. Building 704 and 705, however, are shown as being high risk. Building 705 (in dotted line) is given a risk score of 64.8, and people are advised to avoid this building for now.

The risk scores can also be provided for multiple communities across the borders. In particular, movements of across different communities are taken into account when generating the risk scores. For example, if a large number of members (e.g., exceeding z % of the population) move from a high-risk community A to a low-risk community B, the risk score of community B is adjusted accordingly.

Furthermore, when given permission from the individual members to access certain privacy information, the system can generate personal risk notifications based on health data of the individual members. For example, the system can derive that a member may have underlying conditions (e.g., diabetes or hypertension) based on usage data of insulin pen or smart prescription bottle. Additional health monitoring data collected from the member's mobile sensor devices can also provide insight into the member's health condition. When a member who has underlying health conditions has been close to a known infected case (either based on location or time), the system can provide warnings to the member and/or urge the member to get medical help earlier. The personal data of the individuals, however, remains to be visible to the corresponding members only and is not shared among the communities.

Example Embodiment 3: Efficient Test Pooling

Test pooling is an important public health tool because it allows for more people to be tested quickly using fewer testing resources. Test pooling achieves this by allowing multiple samples to be tested at once in a pool (or a batch). If the pool is positive, samples in the pool can be tested again individually. Alternatively, or in addition, a same sample can be put into multiple pools. When multiple pools produce positive results, it can be determined which sample gives the positive result. Testing pooling allows multiple samples to be run in parallel and fewer tests to be run overall, thereby increasing test efficiency.

The transmission prediction and the behavioral risk scores (e.g., as discussed in Embodiments 1 and 2), along with symptom data given by health providers prior to testing, can be used to determine which and how many tests can be pooled together to produce test results with higher efficiency. In some embodiments, each test sample can be assigned a behavioral risk score based on the community that the sample belongs to (e.g., neighborhood, zip code, county). Samples that are associated with risk scores lower than a particular threshold can be pooled together. The threshold can be predetermined or be adjusted adaptively based on the test results. For example, a range of 0 to 100 risk scores is assigned to the test samples. The threshold is initially set to 20. That is, samples that are associated with risk scores lower than 20 can be pooled together. If all the pools are tested negative, the threshold can be increased to allow a larger number of samples to be pooled together. Once the threshold reaches 50, for example, test results from certain pools begin to turn positive. The system then adaptively reduces the threshold to maintain the proper balance for efficient test pooling.

Figure 8:
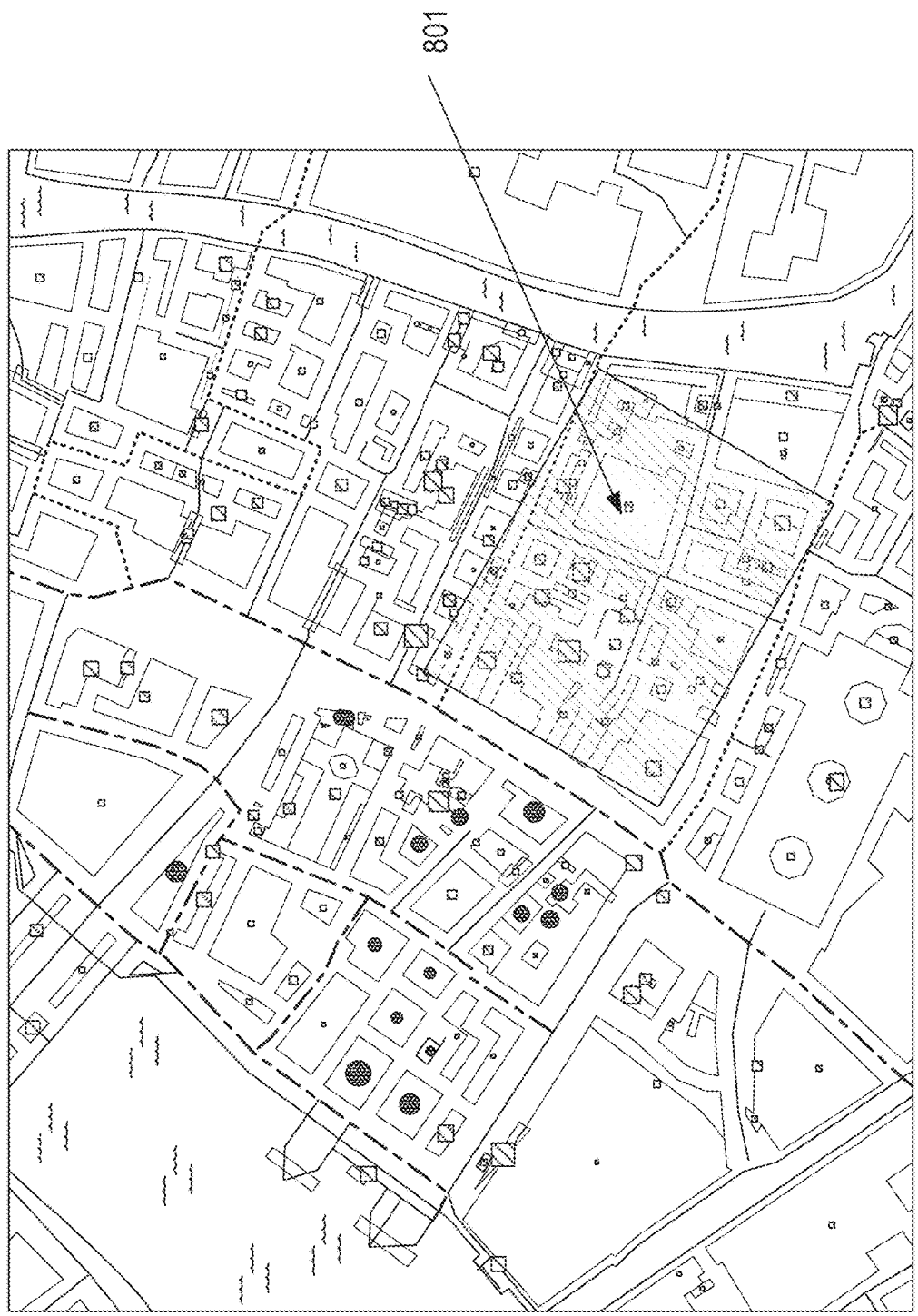
FIG. 8 illustrates an example map of neighborhoods having different risk scores in accordance with the present technology.

FIG. 8 illustrates an example map 800 of neighborhoods having different risk scores in accordance with the present technology. The map 800 shows that neighborhood 801 is a high-risk area. A larger number of samples (e.g., 10 samples or more) from other low risk neighborhoods can be pooled together to be tested. If the pooling result is negative, there is no need to perform additional tests for individual samples in those neighborhoods, thereby saving testing resources. A smaller number of samples from neighborhood 801 should be pooled together because there is a high likelihood of encountering positive samples in that neighborhood.

Example Embodiment 4: Travel/Community Activity Advisory

Figure 9:
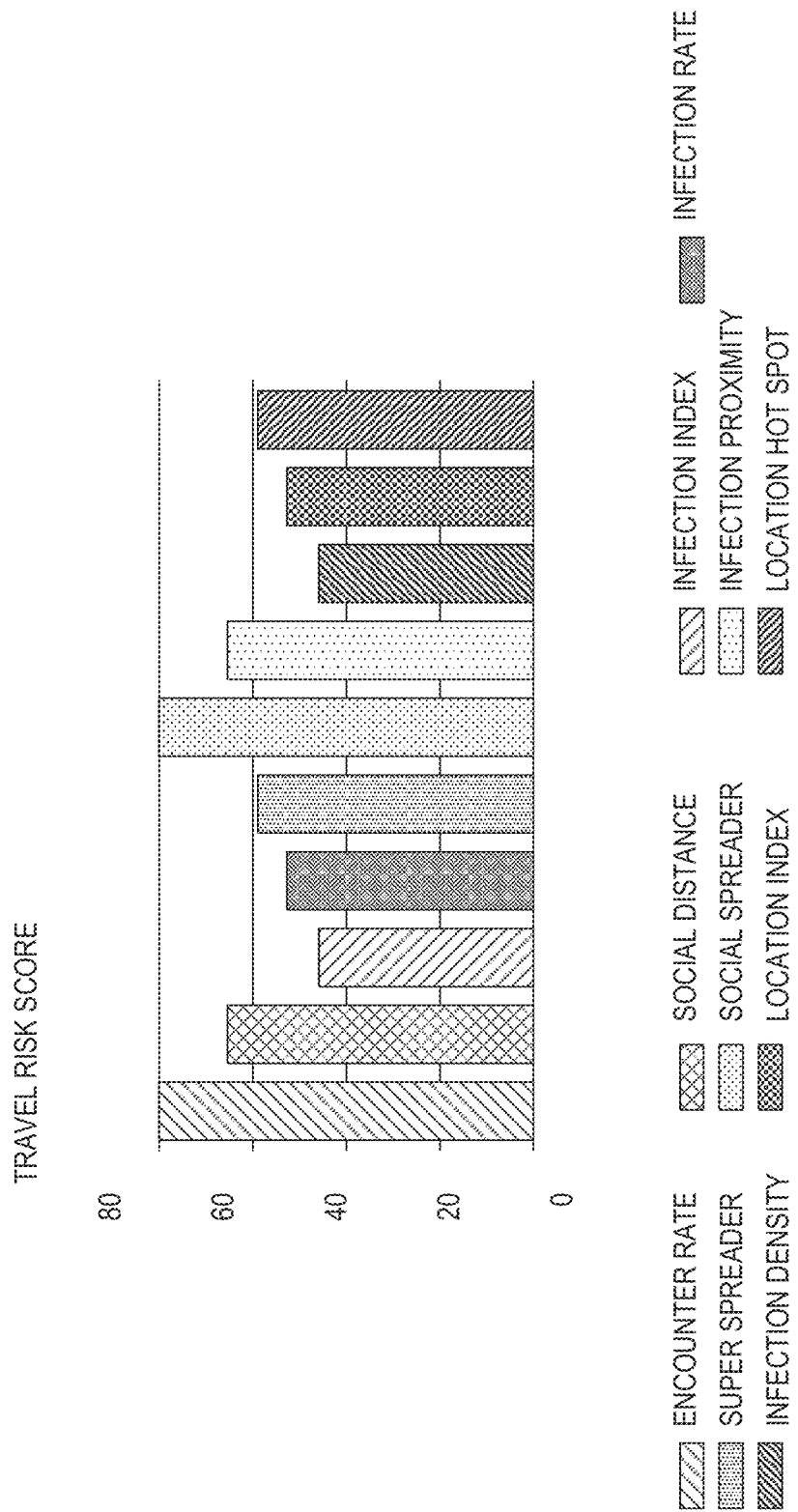
FIG. 9 illustrates an example set of behavioral indicators used to determine travel risk scores in accordance with the present technology.

The transmission prediction and the behavioral risk scores (e.g., as discussed in Embodiments 1 and 2) can also be used to provide travel advisory for community members. For example, a subset of behavioral indicators can be selected to indicate travel risks. FIG. 9 illustrates an example subset of behavioral indicators used to determine travel risk scores in accordance with the present technology. Based on the subset of behavioral indicators, a travel index can be computed for the community to evaluate the level of movement and/or travel activities across the borders of the community. The travel index can be similarly evaluated for other communities so that a travel advisory can be issued with respect to whether travel between other communities and the community is safe. If the travel is considered unsafe, restrictive measures can be applied to contain the spread of the disease.

Within a community, similar indices can be provided to provide advisory regarding community activities, such as shopping, dining, or religious events. Similar to what is shown in FIG. 9, a subset of behavioral indicators can be used to determine risk scores for different types of activities. A corresponding activity index can be computed for the community to evaluate appropriate measures to be taken for performing the corresponding activities.

Figure 10:
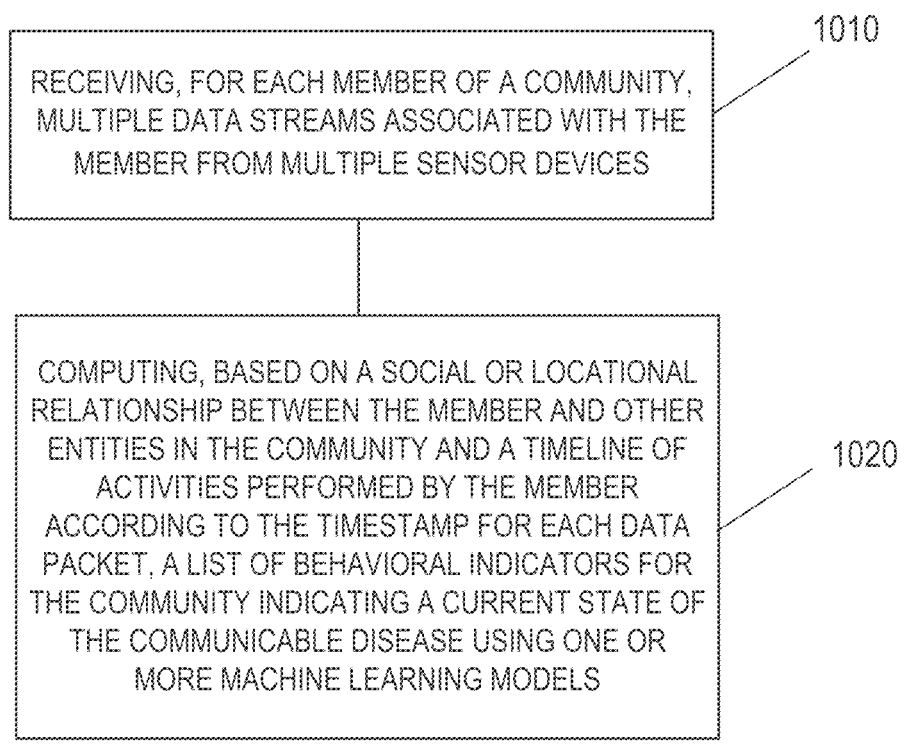
FIG. 10 is a flowchart representation of a method for tracking and predicting a communicable disease in accordance with the present technology.

FIG. 10 is a flowchart representation of a method 1000 for tracking and predicting a communicable disease in accordance with the present technology. The method 1000 includes, at operation 1010, receiving, for each member of a community, multiple data streams associated with the member from multiple sensor devices. A data packet in each of the multiple data streams is associated with a timestamp indicating a time at which the data packet is collected from a corresponding sensor device. The method 1000 also includes, at operation 1020, computing, based on a social or locational relationship between the member and other entities in the community and a timeline of activities performed by the member according to the timestamp for each data packet, a list of behavioral indicators for the community indicating a current state of the communicable disease using one or more machine learning models.

Figure 11:
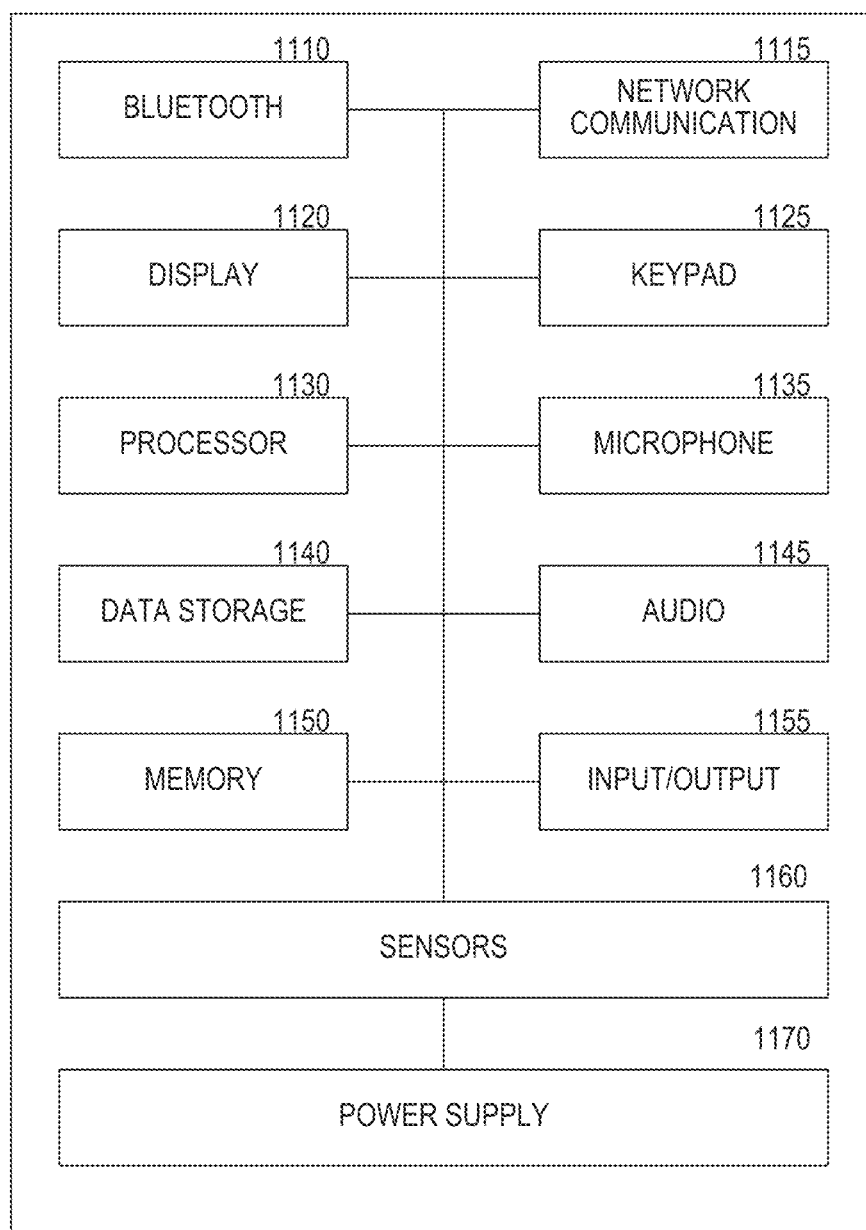
FIG. 11 is a representative block diagram of a sensor device in accordance with embodiments herein.

FIG. 11 is a representative block diagram 1100 of a sensor device in accordance with embodiments herein. Each sensor device may include a processor 1130 for executing processing instructions, a data storage medium component 1140 (e.g., hard drive, flash memory, memory card, etc.), volatile memory and/or nonvolatile memory 1150, a power supply 1170, one or more network interfaces (e.g., Bluetooth Interface 1110; and Network Communication Interface 1115, which enables the sensor device to communicate by transmitting and receiving wireless signals using licensed, semi-licensed or unlicensed spectrum over a telecommunications network). In some embodiments, the sensor device (e.g., a mobile phone) further includes an audio interface 1145, a display 1120, a keypad or keyboard 1125, a microphone 1135, one or more sensors 1160 (e.g., accelerometers, speedometers, engine diagnostic sensors, etc.) that are used to facilitate particular functions of the device, and other input and/or output interfaces 1155. The various components of the sensor devices may be interconnected via one or more buses. The volatile and nonvolatile memories generally include storage media for storing information such as processor-readable instructions, data structures, program modules, or other data. Some examples of information that may be stored include basic input/output systems (BIOS), operating systems, and applications. The stored information may include one or more Session Initiation Protocol (SIP) or Diameter protocol clients capable of generating, transmitting and interpreting syntactically correct SIP or Diameter protocol messages. SIP clients permit the mobile device to register with and communicate via networks such as IMS networks.

Each sensor device may be virtually any device for communicating over a wireless network. Such devices include application servers or mobile telephones, such as Global System for Mobile Communications ("GSM") telephones, Time Division Multiple Access ("TDMA") telephones, Universal Mobile Telecommunications System ("UMTS") telephones, Evolution-Data Optimized ("EVDO") telephones, Long Term Evolution ("LTE") telephones, Generic Access Network ("GAN") telephones, Unlicensed Mobile Access ("UMA") telephones, and other mobile computers or devices, such as Voice over Internet Protocol ("VoIP") devices, Secure User Plane Location ("SUPL") Enabled Terminals (SETs), Personal Digital Assistants ("PDAs"), radio frequency devices, infrared devices, handheld computers, laptop computers, wearable computers, tablet computers, pagers, infotainment systems, vehicle-mounted devices, Internet of Things (loT) devices, and integrated devices combining one or more of the preceding devices, and/or the like.

Each sensor device may connect to a telecommunications network via a trusted radio access network (RAN) or an untrusted RAN. A single user device may be capable of using one or both types of RANs. The RANs may use any wireless communications and data protocol or standard, such as GSM, TDMA, UMTS, EVDO, LTE, GAN, UMA, Code Division Multiple Access ("CDMA") protocols (including IS-95, IS-2000, and IS-856 protocols), Advanced LTE or LTE+, Orthogonal Frequency Division Multiple Access ("OFDM"), General Packet Radio Service ("GPRS"), Enhanced Data GSM Environment ("EDGE"), Advanced Mobile Phone System ("AMPS"), WiMAX protocols (including IEEE 802.16e-2005 and IEEE 802.16m protocols), Wireless Fidelity ("WiFi"), High Speed Packet Access ("HSPA"), (including High Speed Downlink Packet Access ("HSDPA") and High Speed Uplink Packet Access ("HSUPA")), Ultra Mobile Broadband ("UMB"), SUPL, and/or the like.

Figure 12:
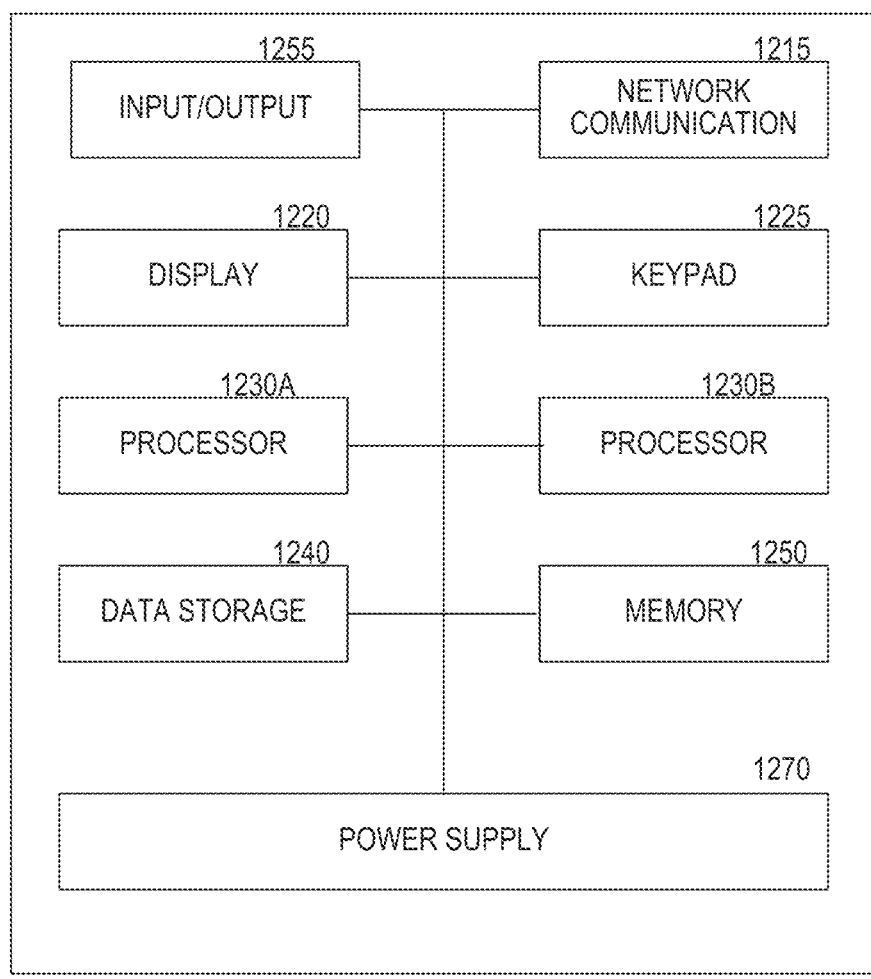
FIG. 12 is a representative block diagram of a decision engine in accordance with embodiments herein.

FIG. 12 is a representative block diagram 1200 of a decision engine in accordance with embodiments herein. The decision engine may include one or more processors (e.g., 1230A, 1230B) for executing processing instructions, a data storage medium component 1240 (e.g., hard drive, flash memory, memory card, etc.), volatile memory and/or nonvolatile memory 1250, a power supply 1270, one or more network interfaces (e.g., Bluetooth Interface 210; and Network Communication Interface 1215, which enables the user device to communicate by transmitting and receiving wireless signals using licensed, semi-licensed or unlicensed spectrum over a telecommunications network). The decision engine can also include a display 1220 and a keypad or keyboard 1225 that are used to facilitate particular functions. The various components of the user devices may be interconnected via one or more buses. The volatile and nonvolatile memories generally include storage media for storing information such as processor-readable instructions, data structures, program modules, or other data. Some examples of information that may be stored include basic input/output systems (BIOS), operating systems, and applications. The stored information may include one or more Session Initiation Protocol (SIP) or Diameter protocol clients capable of generating, transmitting and interpreting syntactically correct SIP or Diameter protocol messages. SIP clients permit the mobile device to register with and communicate via networks such as IMS networks.

It is appreciated that the techniques disclosed herein can be implemented to provide more accurate and meaningful predictions of disease transmissions as well as to identify safe neighborhoods and transmission hotspots, thereby allow the governments and/or officials to make targeted plans to minimize impact of communicable diseases on people's daily lives.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

The invention claimed is:

1. A computer-implemented method for tracking and predicting a communicable disease, comprising:
    sampling data packets from multiple data streams associated with a member from multiple devices at a predefined frequency, wherein the multiple devices include at least one connectivity device configured to provide network connection to at least one of remaining multiple devices, and wherein a data packet in each of the multiple data streams is associated with a timestamp indicating a time at which the data packet is sampled from a corresponding device;
    validating the data packets by discarding data packets that have invalid data fields, wherein an invalid data field is determined according to a type of a data stream associated with the data packet;
    determining a locational entity associated with the member based on how the data packets of the multiple data streams are routed by the at least one connectivity device of the multiple devices,
    determining, using at least one machine learning model that comprises an ensemble of decision trees, a community associated with the locational entity of the member based on the multiple data streams, wherein there exists a social or locational relationship between the member and other entities in the community, and wherein the at least one machine learning model is trained by reinforcing disease-transmission features that are correlated among the ensemble of decision trees; and
    computing, using one or more additional machine learning models based on the social or locational relationship between the member and other entities in the community and a timeline of activities performed by the member according to the timestamp for each data packet, a list of behavioral indicators for the community, wherein the list of behavioral indicators and a corresponding set of epidemiological data of the community indicate a current state of the communicable disease in the community.

2. The method of claim 1, wherein the multiple devices comprise at least a mobile phone, a tablet, a smart watch, a home device, a health monitor, a vehicle, and wherein the connectivity device comprises at least a router, an access pointer, a gateway device, or a base station.

3. The method of claim 1, wherein the multiple data streams comprise at least geolocation data, personal activity data, health data, network connection status data, or device charging status data.

4. The method of claim 1, comprising: adjusting a transmission period for sampling the data packets from the multiple data streams by sending one or more commands to the corresponding device.

5. The method of claim 1, wherein the list of behavioral indicators includes at least one of: a population density within a subarea of the community, a social distancing index, a percentage of people who work at home within the community, a percentage of people who commute to workplaces within the community, an average amount of time people spend outside of their homes, a number of people who commute between two particular locations, a person-to-person encounter rate, a likelihood of encountering an infected person, a percentage of super spreaders in the community, a percentage of social spreaders in the community, a percentage of population who traveled outside of the community, or a quarantine index for members who have recently traveled.

6. The method of claim 1, further comprising:
predicting, based on the list of behavioral indicators, a transmission trend for the communicable disease.

7. The method of claim 6, further comprising:
generating a visualization of the predicted transmission trend; and
presenting the visualization on at least one of the multiple devices associated with a member in the community.

8. The method of claim 6, further comprising:
generating, based on the predicted transmission trend, a future transmission risk score for the community.

9. The method of claim 1, further comprising:
generating, based on the list of behavioral indicators for the community, a current risk score for the community.

10. The method of claim 1, further comprising:
collecting test samples taken from at least a subset of members of the community;
determining, based on the list of behavioral indicators for the community, a risk score associated with each of the test samples; and
determining, based on the risk score associated with each of the test samples, a number of samples to be pooled together for a single test run.

11. The method of claim 10, further comprising:
selecting a sample from the test samples, wherein the sample is determined to be pooled for the single test run in case the risk score associated with the sample is lower than or equal to a threshold.

12. The method of claim 11, further comprising:
determining a result of the single test run; and
adaptively adjusting the threshold based on the result.

13. The method of claim 1, further comprising:
determining a travel index of the community based on a subset of behavioral indicators selected from the list of behavior predictors, wherein the subset of behavioral indicators is associated with movement of the members across a border of the community;
making a recommendation with respect to travel between the community and a second community based on the travel index.

14. The method of claim 1, further comprising:
determining an activity index of the community based on a subset of behavioral indicators selected from the list of behavior predictors, wherein the subset of behavioral indicators is associated with a number of members performing an activity at a designated place;
making a recommendation with respect to the activity based on the activity index.

15. A system for predicting a transmission trend of a communicable disease, comprising one or more processors configured to:
receive a set of epidemiological data of the communicable disease;
sample, for each member of a community, data packets from multiple data streams associated with the member from multiple devices at a predefined frequency, wherein the multiple devices include at least one connectivity device configured to provide network connection to at least one of remaining multiple devices, and wherein the sampled data packets of the multiple data streams are validated consolidated to form behavioral timelines of members in the community;
determine at least one locational entity associated with each member based on how the data packets of the multiple data streams are routed by the at least one connectivity device,
determine, using at least one machine learning model that comprises an ensemble of decision trees, the community associated with the at least one locational entity of each member based on the multiple data streams, wherein there exists a social or locational relationship between the member and other entities in the community, and wherein the at least one machine learning model is trained by reinforcing disease-transmission features that are correlated among the ensemble of decision trees;
determine, using one or more additional machine learning models, a list of behavioral indicators that indicates a current state of the communicable disease in the community based on the behavioral timelines of members in the community; and
predict the transmission trend of the communicable disease within the community based on the list of behavioral indicators and the set of epidemiological data.

16. The system of claim 15, wherein the one or more processors are further configured to:
present the transmission trend on at least one of the multiple devices associated with a member in the community.

17. The system of claim 15, wherein the list of behavioral indicators includes at least one of a population density within a subarea of the community, a social distancing index, a percentage of people who work at home within the community, a percentage of people who commute to workplaces within the community, an average amount of time people spend outside of their homes, a number of people who commute between two particular locations, a person-to-person encounter rate, a likelihood of encountering an infected person, a percentage of super spreaders in the community, a percentage of social spreaders in the community, a percentage of population who traveled outside of the community, or a quarantine index for members who have recently traveled.

18. The system of claim 15, wherein the multiple devices comprise at least a mobile phone, a tablet, a smart watch, a home device, a health monitor, a vehicle, wherein the connectivity device comprises at least a router, an access pointer, a gateway device, or a base station, and wherein the multiple data streams comprise at least geolocation data, personal activity data, health data, network connection status data, or device charging status data.

19. A system for determining transmission risks of a communicable disease in a community, comprising one or more processors configured to:
sample, for each member of the community, data packets from multiple data streams associated with the member from multiple devices at a predefined frequency, wherein the multiple devices include at least one connectivity device configured to provide network connection to at least one of remaining multiple devices, and wherein the multiple data streams are validated and consolidated to form behavioral timelines of members in the community;

determine at least one locational entity associated with each member based on how the data packets of the multiple data streams are routed by the at least one connectivity device;

determine, using at least one machine learning model that comprises an ensemble of decision trees, the community associated with the at least one locational entity of each member based on the multiple data streams, wherein there exists a social or locational relationship between the member and other entities in the community, and wherein the at least one machine learning model is trained by reinforcing disease-transmission features that are correlated among the ensemble of decision trees;

determine, using one or more additional machine learning models, a list of behavioral indicators for the community based on the behavioral timelines of the members in the community; and generate at least one risk score for the community based on the list of behavioral indicators.

20. The system of claim 19, wherein the one or more processors are configured to generate, based on the list of behavioral indicators for the community, a current risk score indicating a current risk level of the community.

21. The system of claim 20, wherein the one or more processors are configured to:
predict a transmission trend of the communicable disease based on the list of behavioral indicators; and
generate, based on the predicted transmission trend, a future transmission risk score indicating an upcoming risk level of the community.

22. The system of claim 19, wherein the multiple devices comprise at least a mobile phone, a tablet, a smart watch, a home device, a health monitor, a vehicle, wherein the connectivity device comprises at least a router, an access pointer, a gateway device, or a base station, and wherein the multiple data streams comprise at least geolocation data, personal activity data, health data, network connection status data, or device charging status data.

23. The system of claim 19, wherein the list of behavioral indicators includes at least one of a population density within a subarea of the community, a social distancing index, a percentage of people who work at home within the community, a percentage of people who commute to workplaces within the community, an average amount of time people spend outside of their homes, a number of people who commute between two particular locations, a person-to-person encounter rate, a likelihood of encountering an infected person, a percentage of super spreaders in the community, a percentage of social spreaders in the community, a percentage of population who traveled outside of the community, or a quarantine index for members who have recently traveled.

24. A system for performing test pooling of a communicable disease in a community, comprising one or more processors configured to:
sample, for each member of the community, data packets from multiple data streams associated with the member from multiple devices at a predefined frequency, wherein the multiple devices include at least one connectivity device configured to provide network connection to at least one of remaining multiple devices, and wherein the multiple data streams are validated and consolidated to form behavioral timelines of members in the community;

determine at least one locational entity associated with each member based on how the data packets of the multiple data streams are routed by the at least the connectivity device of the multiple devices, determine, using at least one machine learning model that comprises an ensemble of decision trees, the community associated with the at least one locational entity of each member based on the multiple data streams, wherein there exists a social or locational relationship between the member and other entities in the community, and wherein the at least one machine learning model is trained by reinforcing disease-transmission features that are correlated among the ensemble of decision trees;

determine, using one or more additional machine learning models, a list of behavioral indicators for the community based on the behavioral timelines of the members in the community;

collect test samples taken from a subset of the members of the community;

determine, based on the list of behavioral indicators for the community, a risk score associated with each of the test samples; and determine, based on the risk score associated with each of the test samples, a number of samples to be pooled together in a single test run for the communication disease.

25. The system of claim 24, wherein the one or more processors are configured to:
select a sample from the test samples, wherein the sample is determined to be pooled for the single test run in case the risk score associated with the sample is lower than or equal to a threshold.

26. The system of claim 25, wherein the one or more processors are configured to:
determine a result of the single test run; and
adaptively adjust the threshold based on the result.

27. The system of claim 24, wherein the multiple devices comprise at least a mobile phone, a tablet, a smart watch, a home device, a health monitor, a vehicle, wherein the connectivity device comprises at least a router, an access pointer, a gateway device, or a base station, and wherein the multiple data streams comprise at least geolocation data, personal activity data, health data, network connection status data, or device charging status data.

28. The system of claim 24, wherein the list of behavioral indicators includes at least one of a population density within a subarea of the community, a social distancing index, a percentage of people who work at home within the community, a percentage of people who commute to workplaces within the community, an average amount of time people spend outside of their homes, a number of people who commute between two particular locations, a person-to-person encounter rate, a likelihood of encountering an infected person, a percentage of super spreaders in the community, a percentage of social spreaders in the community, a percentage of population who traveled outside of the community, or a quarantine index for members who have recently traveled.

* * * * *